United States Patent
Lui et al.

(10) Patent No.: US 8,242,311 B2
(45) Date of Patent: Aug. 14, 2012

(54) PROCESS FOR PREPARING 2,2-DIFLUOROETHYLAMINE AND SALTS THEREOF PROCEEDING FROM DIFLUOROACETONITRILE

(75) Inventors: Norbert Lui, Odenthal (DE); Stefan Antons, Leverkusen (DE); Wahed Ahmed Moradi, Monheim (DE)

(73) Assignee: Bayer Cropscience AG, Monheim (DE)

( * ) Notice: Subject to any disclaimer, the term of this patent is extended or adjusted under 35 U.S.C. 154(b) by 111 days.

(21) Appl. No.: 12/963,738

(22) Filed: Dec. 9, 2010

(65) Prior Publication Data
US 2011/0166388 A1 Jul. 7, 2011

Related U.S. Application Data

(60) Provisional application No. 61/286,607, filed on Dec. 15, 2009.

(30) Foreign Application Priority Data

Dec. 11, 2009 (EP) .................... 09178860

(51) Int. Cl.
C07C 209/48 (2006.01)
C07C 209/62 (2006.01)
(52) U.S. Cl. ......... 564/493; 564/182; 564/215; 564/488
(58) Field of Classification Search ............. 564/488, 564/493
See application file for complete search history.

(56) References Cited

U.S. PATENT DOCUMENTS
4,030,994 A 6/1977 Kollonitsch

OTHER PUBLICATIONS

European Search Report Based on EP 09178860.4-1211 Mailed Apr. 6, 2010.

Wodzinska et al.; "PKA-Dependent Formation of Amides in Water From an Acyl Phosphate Monoester and Amines;" J.Org. Chem.; 2008; 73; 4753-4754.

Grunewald et al.; "Application of the Goldilocks Effect to the Design of Potent and Selective Inhibitors of Phenylethanolamine N-Methyltransferase: Balancing PKA and Steric Effects in the Optimization of 3-Methyl-1,2,3,4-Tetrahydroisoquinoline Inhibitors by B-Fluorination;" J. Med. Chem.; 2006; 49; 2939-2953.

Donetti et al.; "N-(Fluoroethyl)(Imidazolylphenyl)Formamidines. The Issue of the Active Species of Mifentidine;" J. Med. Chem.; 1989; 32; 957-961.

Kluger et al.; "Carboxylic Acid Participation in Amide Hydrolysis. Evidence That Separation of a Nonbonded Complex Can Be Rate Determining;" J. Am. Chem. Soc.; 1982; 104; 2891-2897.

Dickey et al.; "Fluorinated Aminoanthraquinone Dyes;" Industrial and Engineering Chemistry; Product and Process Development; 1956; pp. 209-213.

Swarts; "Sur Les Nitriles Des Acides Fluor-ET Difluoracetiques;" Nov. 14, 1922; 13; pp. 364-365.

Gilman et al.; "2,2,2-Trifluoroethylamine and 2,2,2-Trifluorodiazoethane;" Braun. Ann.; 1943; 65(8); pp. 1458-1460.

*Primary Examiner* — Brian J Davis
(74) *Attorney, Agent, or Firm* — Baker Donelson Bearman, Caldwell & Berkowitz, PC

(57) ABSTRACT

The present invention relates to a process for preparing 2,2-difluoroethylamine of the formula (I) and salts thereof, for example sulphates, hydrochlorides or acetates, which proceeds from difluoroacetonitrile.

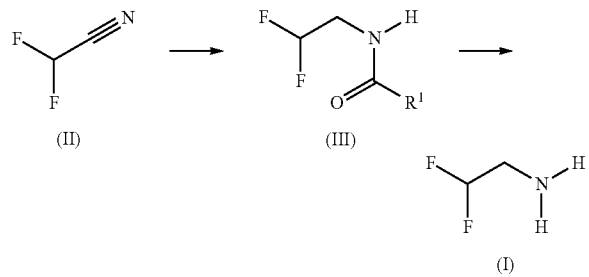

10 Claims, No Drawings

PROCESS FOR PREPARING 2,2-DIFLUOROETHYLAMINE AND SALTS THEREOF PROCEEDING FROM DIFLUOROACETONITRILE

CROSS REFERENCE TO RELATED APPLICATIONS

This application claims priority from EP Application 09178860.4 filed Dec. 11, 2009, and U.S. application Ser. No. 61/286,607 filed Dec. 15, 2009, the contents of which are incorporated herein by reference in their entireties.

BACKGROUND OF THE INVENTION

1. Field of the Invention

The present invention relates to a process for preparing 2,2-difluoroethylamine of the formula (I) and salts thereof, for example sulphates, hydrochlorides or acetates, which proceeds from difluoroacetonitrile.

2. Description of Related Art 2,2-Difluoroethylamines and salts thereof are important intermediates for preparation of active ingredients, especially active agrochemical ingredients. Various preparation methods for 2,2-difluoroethylamine are known.

Donetti et al. (*J. Med. Chem.* 1989, 32, 957-961) describe, for example, the synthesis of 2,2-difluoroethylamine hydrochloride proceeding from 2,2-difluoroacetamide, in which the corresponding amide is reduced with a diboran solution in tetrahydrofuran (THF). Kluger et al. describe, in *JACS* 1982, 104, 10, 2891-2897, the reduction of 2,2-difluoroacetamide with sodium boranate and boron trifluoride etherate to give 2,2-difluoroethylamine.

The low yield and the use of expensive and hazardous chemicals, for example sodium boranate/$BF_3$ or diborane, prevent the processes according to Donetti et al. and Kluger et al. from being suitable for the industrial scale preparation of 2,2-difluoroethylamine. All these processes are uneconomic, and industrial scale implementation is associated with high costs.

An inexpensive preparation process consists in the hydrogenation of difluoroacetonitrile, which is readily available as a starting material. It can be prepared, for example, from difluoroacetamide (Swarts et al., *Bulletin des Societes Chimiques Belges* 1922, 31, 364-5, Grunewald et al., *J. Med. Chem.* 2006, 49 (10), 2939-2952). The catalytic hydrogenation of trifluoroacetonitrile using $PtO_2$ has been described by Gilman et al. (*JACS* 1943, 65 (8), 1458-1460), to obtain trifluoroethylamine hydrochloride.

The inventors have now found that the process described for trifluoroacetonitrile by Gilman et al. is unsuitable for the hydrogenation of difluoroacetonitrile. When the hydrogenation of difluoroacetonitrile is performed under the conditions described, 2,2-difluoroethylamine is obtained only in traces, whereas a multitude of more highly alkylated reaction products is otherwise obtained.

In addition, it has been found that the catalytic hydrogenation of difluoroacetonitrile in pure glacial acetic acid or in toluene does afford difluoroethylamine, but the conversions were unselective and the product was not isolable from the reaction mixture owing to the low boiling point.

SUMMARY OF THE INVENTION

It is therefore an object of the present invention to provide a process with which difluoroacetonitrile can be converted to 2,2-difluoroethylamine selectively and in good yields. It has now been found that 2,2-difluoroethylamine of the formula (I) can be obtained by first reducing difluoroacetonitrile of the formula (II) in a first step by catalytic hydrogenation to the N-(2,2-difluoroethyl)amide of the formula (III), and then converting the N-(2,2-difluoroethyl)amide thus obtained to 2,2-difluoroethylamine by treatment with acid. The reaction is illustrated in the reaction scheme below, where $R^1$ may be as defined below.

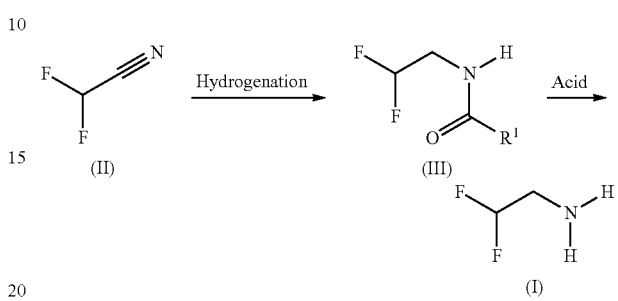

The present invention thus relates to a process for preparing 2,2-difluoroethylamine of the formula (I), comprising the following reaction steps:

(a) catalytic hydrogenating difluoroacetonitrile of the formula (II) to the corresponding amide of the formula (III)

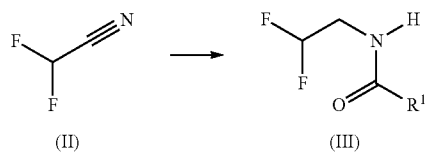

where
$R^1$ is H, $C_{1-12}$-alkyl, $C_{3-8}$-cycloalkyl, $C_{1-12}$-haloalkyl, aryl (e.g. phenyl), $C_{1-12}$-alkyl-$C_{6-10}$-aryl, wherein $R^1$ is preferably H, methyl, trifluoromethyl, ethyl, n-propyl, isopropyl, n-butyl, isobutyl, sec-butyl, and t-butyl, n-pentyl, n-hexyl, 1,3-dimethylbutyl, 3,3-dimethylbutyl, n-heptyl, n-nonyl, n-decyl, n-undecyl, n-dodecyl, phenyl or benzyl, more preferably H, methyl, t-butyl or phenyl,
in the presence of an organic acid of the general formula (IVa), of an acid chloride of the general formula (IVb) or acid anhydride of the general formula (IVc)

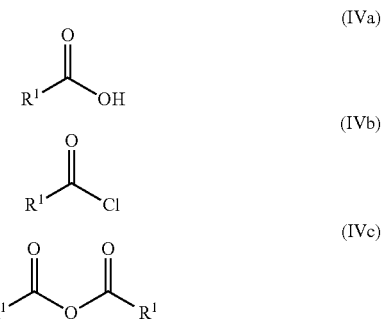

or a mixture thereof, where $R^1$ is as defined above, preferably in the presence of $CF_3COOH$, $CH_3COOH$, $CH_3COCl$, benzoyl chloride, acetic anhydride, pivalic anhydride, t-butylacetic anhydride, trifluoroacetic anhydride or benzoic anhydride, or mixtures thereof, more preferably in the presence of CH₃COOH, CH₃COCl or acetic anhydride or a mixture thereof; and (b) converting the difluoroethylamide of the formula (III) to 2,2-difluoroethylamine of the formula (I) by adding an acid which is suitable for cleaving the difluoroethylamide

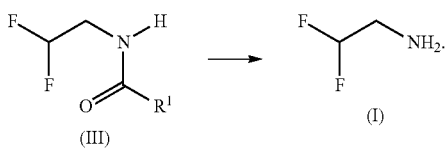

The invention further relates to the difluoroethylamide intermediate of the general formula (III) as defined above, which is obtained by the process according to the invention.

DETAILED DESCRIPTION OF A PREFERRED EMBODIMENT

The inventive catalytic hydrogenation in step (a) takes place in the presence of a catalyst, with gaseous hydrogen being introduced into the reaction vessel or being generated in situ in the reaction vessel by the use of formic acid or hydrazine and the derivatives or salts thereof.

For the inventive catalytic hydrogenation in reaction step (a), the catalyst used may be any catalyst which is suitable for catalytic hydrogenation and is known to those skilled in the art. Useful examples include palladium catalysts, platinum catalysts, Raney nickel catalysts, Lindlar catalysts, ruthenium catalysts and rhodium catalysts. In addition to these heterogeneous catalysts, it is also possible to use homogeneous catalysts. Suitable catalysts preferably contain one or more metals of groups 8-10 of the Periodic Table, especially one or more metals selected from iron, ruthenium, osmium, cobalt, rhodium, iridium, nickel, palladium and platinum. The metals may be present in any chemical form, for example in elemental, colloidal, salt or oxide form, together with complexing agents as chelates, or as alloys, in which case the alloys may also include other metals, for example aluminium, as well as the metals listed above. The metals may be present in supported form, i.e. applied to any support, preferably an inorganic support. Examples of suitable supports are carbon (charcoal or activated carbon), aluminium oxide, silicon dioxide, zirconium dioxide or titanium dioxide. Catalysts preferred in accordance with the invention contain one or more metals of groups 8-10 of the Periodic Table on an inorganic support. Particular preference is given in accordance with the invention to catalysts which include platinum and/or palladium, and are optionally applied to an inorganic support. Such catalysts are, for example, PtO₂, Pd(OH)₂ on activated carbon (Pearlman catalyst), Raney nickel and Lindlar catalysts.

In the process according to the invention, the catalyst is used, based on the difluoroacetonitrile used, in a concentration of about 0.01 to about 30% by weight. The catalyst is preferably used in a concentration of about 0.1 to about 12% by weight, more preferably of about 0.1 to about 2% by weight.

In step (a) of the process according to the invention, it is usual to initially charge difluoroacetonitrile and the catalyst with the organic acid, acid chloride, acid anhydride or mixture thereof in a first step (i), and to introduce hydrogen or generate it in situ in a second step (ii). The reversal of steps (i) and (ii) is possible. It is also possible to hydrogenate continuously or batchwise.

The catalytic hydrogenation can be performed under elevated pressure (i.e. up to about 200 bar) in an autoclave, or at standard pressure in a hydrogen gas atmosphere. Especially at high reaction temperatures, it may be helpful to work at elevated pressure. The (additional) pressure increase can be brought about by supply of an inert gas, such as nitrogen or argon. The inventive hydrogenation is effected preferably at a pressure in the range from about 1 to about 100 bar, more preferably at a pressure in the range from about 5 to about 25 bar.

The organic acid, acid chloride or acid anhydride, or mixture thereof, present in reaction step (a) causes the difluoroethylamine formed to be removed from the hydrogenation process, rather than reacting to give (CF₂HCH₂)₂NH.

The necessary amount of the organic acid, acid chloride or acid anhydride present in reaction step (a), based on difluoroacetonitrile, can be determined by the person skilled in the art in a simple manner by routine tests. The molar ratio of difluoroacetonitrile to the organic acid, acid chloride or acid anhydride used, or mixture thereof, may, for example, be about 0.5 to 10, or about 0.9 to 2. A ratio of about 1 to 1.1 is preferred. The use of greater amounts of organic acid, acid chloride or acid anhydride or a mixture thereof is possible in principle, but is disadvantageous for economic reasons.

Preferred reaction temperatures for the hydrogenation in reaction step (a) range from –20° C. to 100° C., preference being given to temperatures of 0° C. to 40° C.

The reaction time of the hydrogenation is generally 30 minutes to 24 hours, though shorter or longer reaction times do not have an adverse effect.

In the inventive reaction step (b), the amide of the formula (III) is reacted with a suitable acid to give the 2,2-difluoroamine.

After reaction step (a), the amide of the formula (III) can also be isolated by removing the catalyst and the solvent, if present, and sent to reaction step (b).

The acids useable in reaction step (b) are selected from phosphoric acid (H₃PO₄), sulphuric acid (H₂SO₄), hydrochloric acid (HCl), hydrobromic acid (HBr), hydrofluoric acid (HF), potassium hydrogensulphate (KHSO₄), CF₃COOH, CF₃SO₃H, CH₃COOH, and p-toluenesulphonic acid.

Preferred reaction temperatures for the cleavage of the difluoroamide of the formula (III) in reaction step (b) range from about 0° C. to about 100° C.

It is generally advantageous to perform the process according to the invention in the presence of solvents (diluents). However, the catalytic hydrogenation can also be performed without a solvent. Solvents are advantageously used in such an amount that the reaction mixture remains efficiently stirrable over the entire process. Advantageously, based on the difluoroacetonitrile used, 1 to 50 times the amount of solvent, preferably 2 to 40 times the amount of solvent and more preferably 2 to 30 times the amount of solvent is used.

Useful solvents for performance of the process according to the invention include all organic solvents which are inert under the reaction conditions, the type of solvent used depending on the type of reaction procedure, more particularly on the type of catalyst used and/or the hydrogen source (introduction of gaseous hydrogen or generation in situ). Solvents are also understood in accordance with the invention to mean mixtures of pure solvents.

Solvents suitable in accordance with the invention are especially ethers, such as ethyl propyl ether, n-butyl ether, anisol, phenetol, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, and polyethers of ethylene oxide and/or propylene oxide; aliphatic, cycloaliphatic or aromatic hydrocarbons such as pentane, hexane, heptane, octane, nonane, and technical-grade hydrocarbons which may be substituted by fluorine and chlorine atoms, such as methylene chloride, dichloromethane, trichloromethane, carbon tetrachloride, fluorobenzene, chlorobenzene or dichlorobenzene; for example white spirits having components with boiling points in the range, for example, from 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, xylene; esters such as methyl acetate, ethyl acetate, butyl acetate, isobutyl acetate, and also dimethylcarbonate, dibutylcarbonate or ethylenecarbonate. Organic acids such as formic acid or acetic acid. The inventive solvent used may also be water. In reaction step (a), the organic acid, the acid chloride or anhydride, or mixtures thereof, present in the reaction, may also be used as the solvent.

Solvents preferred in accordance with the invention in reaction step (a) are toluene, tetrahydrofuran, methyltetrahydrofuran or mixtures thereof.

In reaction step (b), water is preferred as the inventive solvent.

The workup and purification can be effected via the free amine or via salts thereof. When the 2,2-difluoroethylamine is present in free form after the process according to the invention, it is purified by distillation if necessary. When 2,2-difluoroethylamine is present as a salt, it is then purified if necessary, preferably by crystallization. Preferred salts are, for example, sulphates, hydrochlorides or acetates.

Water-soluble salts of 2,2-difluoroethylamine are generally purified by extraction from an aqueous solution. The free 2,2-difluoroethylamine is released by reacting the corresponding salt with organic or inorganic bases (e.g. $NaHCO_3$, $Na_2CO_3$ or NaOH). Subsequently, the difluoroethylamine is distilled directly out of the aqueous solution or extracted into an organic solvent.

The present invention is illustrated in detail by the examples which follow, though the examples should not be interpreted so as to restrict the invention.

PREPARATION EXAMPLES

Synthesis of N-(2,2-difluoroethyl)acetamide 20 g (0.259 mol) of difluoroacetonitrile and 26.5 g (0.259 mol) of acetic anhydride are dissolved in 242 ml of tetrahydrofuran and hydrogenated over 0.66 g (0.31 mmol) of palladium on activated carbon (5% Pd) with 50 bar of hydrogen until the pressure is constant. The autoclave is cooled, such that the reaction temperature does not rise above 20° C. The reaction mixture is filtered through kieselguhr. After the solvent has been removed 34.9 g (GC-MS purity 75.5%) of N-(2,2-difluoroethyl)acetamide are obtained.

$^1$H NMR (400 MHz, $d_6$-DMSO): 8.24 (1H, sb, NH), 5.98 (1H, dt, $^3J_{HF}$=60 Hz; $^3J_{HH}$=3.9 Hz), 3.56-3.49 (2H, m), 1.87 (3H, s).

$^{13}$C NMR (600 MHz, $d_6$-THF): 171.7 (CO), 115.3 ($CHF_2$), 42.5 ($CH_2$), 22.3 ($CH_3$).

$^{19}$F NMR (376 MHz, $D_2O$, $CFCl_3$ internal standard): −121.3 (dt, $^2J_{FH}$=56.1 Hz; $^3J_{FH}$=16.1 Hz).

Synthesis of 2,2-difluoroethylamine hydrochloride 10 g (81.23 mmol) of N-(2,2-difluoroethyl)acetamide are initially charged in 16 g of water and admixed with 18.5 g (162.5 mmol, 32%) of hydrochloric acid. The reaction mixture is stirred at 90° C. for 1 hour and cooled to room temperature, and then the solvent is removed. The residue is azeotroped with toluene. This gives 8.70 g of 2,2-difluoroethylamine hydrochloride (91.1% yield based on N-(2,2-difluoroethyl)acetamide).

$^1$H NMR (400 MHz, $D_2O$): 6.31 (1H, dt, $^3J_{HF}$=53.34 Hz; $^3J_{HH}$=2.6 Hz), 3.52 (2H, dt, $^3J_{HF}$=16.32 Hz; $^3J_{HH}$=2.6 Hz).

The invention claimed is:

1. A process for preparing 2,2-difluoroethylamine of formula (I), comprising:
   (a) catalytically hydrogenating difluoroacetonitrile of formula (II) to a difluoroethylamide of formula (III)

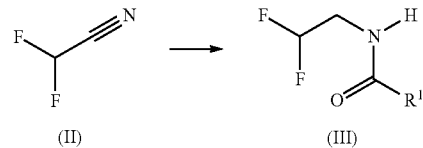

where
   $R^1$ is H, $C_{1-12}$-alkyl, $C_{3-8}$-cycloalkyl, $C_{1-12}$-haloalkyl, aryl, $C_{1-12}$-alkyl-$C_{6-10}$-aryl,
   in the presence of an organic acid of formula (IVa), of an acid chloride of formula (IVb) or an acid anhydride of formula (IVc), or a mixture thereof,

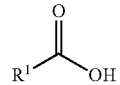

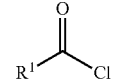

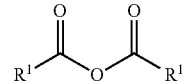

where $R^1$ is as defined above; and
   (b) converting the difluoroethylamide of formula (III) to 2,2-difluoroethylamine by adding an acid which is suitable for cleaving the difluoroethylamide

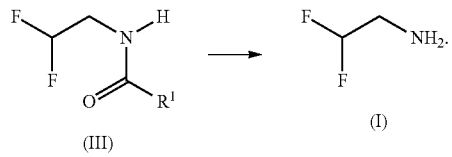

2. A process according to claim 1, wherein $R^1$ is H, methyl, trifluoromethyl, ethyl, n-propyl, isopropyl, n-butyl, isobutyl, sec-butyl, t-butyl, n-pentyl, n-hexyl, 1,3-dimethylbutyl, 3,3-dimethylbutyl, n-heptyl, n-nonyl, n-decyl, n-undecyl, n-dodecyl, phenyl or benzyl.

3. A process according to claim 1, wherein the acid present in (a) is present in a molar ratio of difluoroacetonitrile to the organic acid of 0.5 to 10.

4. A process according to claim 1, wherein (a) and (b) are performed without isolation of difluoroethylamide of formula (III).

5. A process according to claim 1, wherein the catalytic hydrogenation of (a) comprises using a catalyst comprising palladium, platinum, Raney nickel or rhodium.

6. A process according to claim 1, wherein catalytic hydrogenation involves introducing gaseous hydrogen into a reaction vessel and/or producing gaseous hydrogen in situ.

7. A process according to claim 1, wherein the acid which is suitable for cleaving the difluoroethylamide of (b) is selected from the group consisting of $H_3PO_4$, $H_2SO_4$, HCl, HBr, HF, $KHSO_4$, $CF_3COOH$, $CF_3SO_3H$, $CH_3COOH$ and p-toluenesulphonic acid.

8. Difluoroethylamide of formula (III) which is suitable for use in the process as defined in claim 1

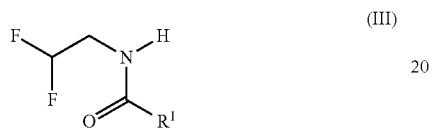

in which
R$^1$ is H, $C_{1-12}$-alkyl, $C_{3-8}$-cycloalkyl, $C_{1-12}$-haloalkyl, $C_{1-12}$-alkyl-$C_{6-10}$-aryl.

9. Difluoroethylamide of formula (III) according to claim 8, in which
R$^1$ is H, methyl, trifluoromethyl, ethyl, n-propyl, isopropyl, n-butyl, isobutyl, sec-butyl, t-butyl, n-pentyl, n-hexyl, 1,3-dimethylbutyl, 3,3-dimethylbutyl, n-heptyl, n-nonyl, n-decyl, n-undecyl, n-dodecyl, or benzyl.

10. A compound of formula (III) which has been obtained by catalytically hydrogenating difluoroacetonitrile of formula (II) to a difluoroethylamide of formula (III)

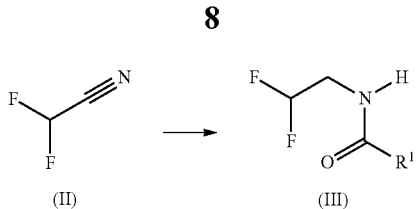

where
R$^1$ is H, $C_{1-12}$-alkyl, $C_{3-8}$-cycloalkyl, $C_{1-12}$-haloalkyl, aryl, $C_{1-12}$-alkyl-$C_{6-10}$-aryl,
in the presence of an organic acid of formula (IVa), of an acid chloride of formula (IVb) or an acid anhydride of formula (IVc), or a mixture thereof,

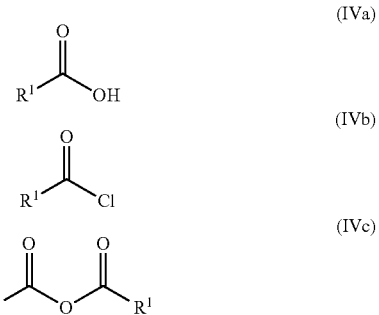

where R$^1$ is as defined above.

* * * * *